US012691294B2

(12) United States Patent
Dinh et al.

(10) Patent No.:    US 12,691,294 B2
(45) Date of Patent:        Jul. 28, 2026

(54) SELECTIVELY ENABLING FILTERING FOR PHYSIOLOGICAL PARAMETERS

(71) Applicant: Stryker Corporation, Kalamazoo, MI (US)

(72) Inventors: Doan Huu Dinh, Seattle, WA (US); Tyson G. Taylor, Bothell, WA (US)

(73) Assignee: Stryker Corporation, Portage, MI (US)

( * ) Notice: Subject to any disclaimer, the term of this patent is extended or adjusted under 35 U.S.C. 154(b) by 483 days.

(21) Appl. No.: 18/373,100

(22) Filed:     Sep. 26, 2023

(65) Prior Publication Data

US 2024/0100347 A1      Mar. 28, 2024

Related U.S. Application Data

(60) Provisional application No. 63/410,148, filed on Sep. 26, 2022.

(51) Int. Cl.
A61B 5/0205        (2006.01)
A61B 5/00        (2006.01)
(Continued)

(52) U.S. Cl.
CPC ........ A61N 1/3925 (2013.01); A61B 5/02055 (2013.01); A61B 5/332 (2021.01); A61B 5/339 (2021.01); A61B 5/361 (2021.01); A61B 5/4836 (2013.01); A61B 5/7225 (2013.01); A61B 5/725 (2013.01); A61B 5/7282 (2013.01); A61B 5/742 (2013.01); A61B 5/7475 (2013.01); A61H 31/006 (2013.01); A61N 1/39044 (2017.08); A61N 1/395 (2013.01); A61N 1/3993 (2013.01);
(Continued)

(58) Field of Classification Search
None
See application file for complete search history.

(56) References Cited

U.S. PATENT DOCUMENTS 10,828,232 B2    11/2020  Freeman et al.
10,905,344 B2     2/2021  Sullivan et al.
(Continued)

FOREIGN PATENT DOCUMENTS

AU        2009202971 B2     8/2009
AU        2020218863 A1     8/2021
(Continued)

OTHER PUBLICATIONS

Examination Report (Communication pursuant to Article 94(3) EPC) for European Application No. 23199825.3, dated Oct. 23, 2024, 8 pages.
(Continued)

*Primary Examiner* — Levon J Shahinian
(74) *Attorney, Agent, or Firm* — Lee & Hayes, P.C.

(57)        ABSTRACT

An example method is performed by a first medical device and includes generating first data indicating a physiological parameter of a subject; generating a filter configured to remove an artifact associated with a treatment; and generating second data by applying the filter to the first data. The example method further includes determining that a second medical device is administering the treatment to the subject. In response to determining that the second medical device is administering the treatment to the subject, the first medical device outputs an indication that filtering is available; receives an input signal selecting the filtering; and in response to receiving the input signal, displays the second data.

20 Claims, 6 Drawing Sheets

(51) Int. Cl.

| | |
|---|---|
| *A61B 5/332* | (2021.01) |
| *A61B 5/339* | (2021.01) |
| *A61B 5/361* | (2021.01) |
| *A61H 31/00* | (2006.01) |
| *A61N 1/39* | (2006.01) |

(52) U.S. Cl.
   CPC .. *A61H 2201/10* (2013.01); *A61H 2201/5043*
   (2013.01); *A61H 2230/065* (2013.01)

(56) References Cited

U.S. PATENT DOCUMENTS

| | | |
|---|---|---|
| 10,905,348 B2 | 2/2021 | Grunwald et al. |
| 10,987,012 B2 | 4/2021 | Quan et al. |
| 11,172,862 B2 | 11/2021 | Tan et al. |
| 11,278,201 B2 | 3/2022 | Thomson et al. |
| 2009/0149749 A1 | 6/2009 | Heron |
| 2015/0088020 A1 | 3/2015 | Dreisbach et al. |
| 2018/0177678 A1 | 6/2018 | Wijshoff et al. |
| 2019/0255340 A1 | 8/2019 | Freeman et al. |
| 2021/0015387 A1 | 1/2021 | Sullivan et al. |
| 2022/0039725 A1 | 2/2022 | Sullivan |
| 2024/0099642 A1 | 3/2024 | Dinh et al. |

FOREIGN PATENT DOCUMENTS

| | | |
|---|---|---|
| EP | 2849628 B1 | 7/2016 |
| JP | 6080021 B2 | 2/2017 |

OTHER PUBLICATIONS

Examination Report (Communication pursuant to Article 94(3) EPC) for European Application No. 23199845.1, dated Oct. 24, 2024, 7 pages.
Extended European Search Report for EP Application No. 23199825.3, dated Feb. 20, 2024, 9 pages.
Extended European Search Report for EP Application No. 23199845.1, dated Feb. 20, 2024, 9 pages.
Summons to Attend Oral Proceedings for European Application No. 23199825.3, dated Feb. 21, 2025, 8 pages.
Summons to Attend Oral Proceedings for European Application No. 23199845.1, dated Mar. 14, 2025, 7 pages.
Satija, et al., "A Review of Signal Processing Techniques for Electrocardiogram Signal Quality Assessment," IEEE Reviews in Biomedical Engineering, vol. 11, Feb. 28, 2018, pp. 36-52.

NON-
EMPHASIZED
LINE

EMPHASIZED
LINE

FIG. 2A

NON-
EMPHASIZED
LINE

EMPHASIZED
LINE

FIG. 2B

NON-
EMPHASIZED
LINE

EMPHASIZED
LINE

FIG. 2C

Filtering Available

SELECT

UNFILTERED
WAVEFORM
302

SELECTABLE
OPTION
304

NOTIFICATION
404

Filtering Active

FILTERED
WAVEFORM
402

NOTIFICATION
406

500

600

SELECTIVELY ENABLING FILTERING FOR PHYSIOLOGICAL PARAMETERS

CROSS-REFERENCE TO RELATED APPLICATION

This application claims priority to U.S. Provisional App. No. 63/410,148, which was filed on Sep. 26, 2022 and is incorporated by reference herein in its entirety.

BACKGROUND

Medical devices can be used to facilitate patient monitoring, facilitate patient treatments, or a combination of both. In some environments, multiple medical devices are located in close proximity to one another. Some may be monitoring and/or treating the same patient, and some may be monitoring and/or treating different patients. In some cases, one medical device is administering a treatment that causes an artifact in a physiological parameter detected by another medical device.

BRIEF DESCRIPTION OF THE DRAWINGS

FIGS. 2A to 2C illustrate different examples of emphasized lines.

DETAILED DESCRIPTION

Various implementations described herein relate to a monitoring device generating filtered data by removing an artifact in unfiltered data indicative of a physiological parameter detected by the monitoring device, wherein the artifact is caused by a treatment administered by a treating device. In particular cases, the monitoring device selectively displays the unfiltered data when one or more predetermined conditions are satisfied. In some examples, the monitoring device provides an option for displaying the filtered data to a user when the predetermined condition(s) are satisfied.

Various medical devices are configured to perform artifact removal and/or filtering of data indicative of physiological parameters. In particular examples, a monitor-defibrillator removes a chest compression artifact from an electrocardiogram (ECG) of a patient. In many cases, the filtered data enables the medical device and/or a user (e.g., a rescuer or clinician) to more accurately assess the patient's condition. However, in some cases, the filtered data actually obscures the patient's condition. For instance, the filtered data can cause the medical device and/or the user to determine that the patient has a pathologic condition when no pathologic condition is present, or vice versa. Thus, in some cases, the filtered data can prevent the medical device, or the user, from accurately assessing the condition of the patient.

According to implementations of the present disclosure, a medical device outputs the filtered data only when one or more predetermined conditions have been satisfied. These conditions are associated with a relatively high likelihood that the filtered data reliably reflects the condition of the patient. For example, the medical device enables a user to select the filtered data for display only when the medical device determines that the treatment is being actively administered to the patient, such that the filtered data reflects the physiological parameter with a treatment artifact removed. However, the medical device prevents the user from selecting the filtered data for display when the medical device determines that the treatment has paused or is otherwise not being administered to the patient. When the treatment is not being administered, the filtered data may be less indicative of the patient's condition than the unfiltered condition. Thus, the medical device is configured to prevent confusion by the user operating the medical device.

Figure 1:
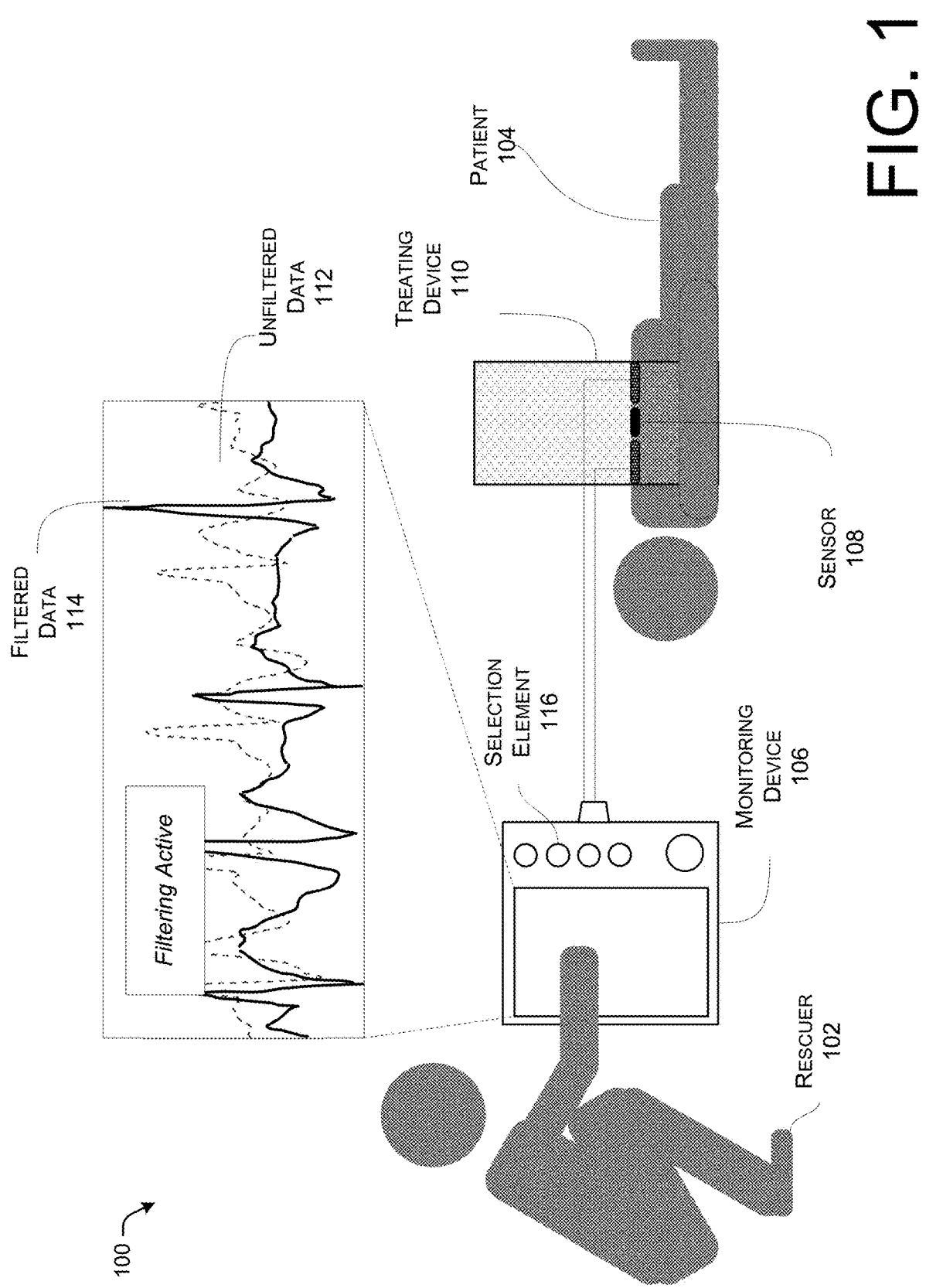
FIG. 1 illustrates an example environment for selectively outputting processed data to a rescuer.

FIG. 1 illustrates an example environment 100 for selectively outputting processed data to a rescuer 102. In various implementations, the environment 100 includes a rescue scene. The rescue scene, for instance, is in a clinical environment (e.g., a hospital) or a non-clinical environment (e.g., the scene of an accident).

In various cases, the rescuer 102 is treating a patient 104. For instance, the rescuer 102 is an EMT professional monitoring and/or treating a medical condition of the patient 104. In some cases, the patient 104 is experiencing cardiac arrest, respiratory arrest, or some other dangerous medical condition.

The rescuer 102 monitors the condition of the patient 104 using a monitoring device 106. For instance, the monitoring device 106 may be a monitor-defibrillator, a medical imaging device, an ultrasound monitor, a standalone ECG monitor, or another type of patient monitor. The monitoring device 106 includes and/or is communicatively coupled to a sensor 108. The sensor 108 is configured to detect at least one physiological parameter of the patient 104. According to various implementations, the signal detected by the sensor 108 is referred to as a "parameter signal." Examples of physiological parameters include, for instance, an ECG, an impedance, a force administered to the patient 104, a blood pressure, an airway parameter (e.g., a partial pressure of carbon dioxide, a partial pressure of oxygen, a capnograph, an end tidal gas parameter, a flow rate, etc.), a blood oxygenation (e.g., a pulse oximetry value, a regional oximetry value, etc.), an electroencephalogram (EEG), a temperature, a heart sound, a blood flow rate, a physiological geometry (e.g., a shape of a blood vessel, an inner ear shape, etc.), a heart rate, a pulse rate, or the like. For example, the sensor 108 includes at least one of electrodes, a detection circuit, defibrillator pads, a force sensor, a blood pressure cuff, an ultrasound-based blood pressure sensor, an invasive (e.g., intra-arterial) blood pressure sensor (e.g., including a cannula inserted into the patient 104), a gas sensor (e.g., a carbon dioxide and/or oxygen sensor), a flowmeter, a pulse oximetry sensor a regional oximetry sensor, a thermometer, a microphone, an ultrasound transducer, a medical imaging device (e.g., an ultrasound imaging device), or the like. In various cases, the monitoring device 106 outputs the physiological parameter(s) to the rescuer 102. For instance, the monitoring device 106 includes a display, a speaker, or haptic feedback device that conveys the physiological parameter(s) to the rescuer 102.

A treating device 110 (also referred to as a "treatment device") administers a treatment to the patient 104. For example, the treating device 110 is a monitor-defibrillator, an automated external defibrillator (AED), mechanical chest compression device, a smart bag-valve mask, a ventilator, a heart-lung machine, an intravenous fluid (IV) pump, or the like. Examples of treatments include defibrillation, pacing, cardioversion, administration of chest compressions, administration of oxygen to the airway of the patient 104, movement of air in the airway of the patient, administration of fluids to the patient 104, extracorporeal membrane oxygenation (ECMO), administration of a medication to the patient 104, or the like. In some implementations, the monitoring device 106 is also configured to administer a treatment to the patient 104. Further, in some cases, the treating device 110 is configured to detect one or more physiological parameters of the patient 104.

The monitoring device 106, in some cases, detects the treatment administered by the treating device 110 by analyzing the parameter signal. For instance, the monitoring device 106 identifies the treatment based on a time, frequency, or shape of an artifact in the parameter signal that corresponds to the treatment. For instance, a chest compression artifact in an ECG can be recognized as a periodic spike in the ECG at a frequency consistent with chest compression administration. In various implementations, the monitoring device 106 identifies the type of device administering the treatment based on the artifact. For example, a chest compression artifact produced one type of mechanical chest compression device is shaped differently than a chest compression artifact produced by another type of mechanical chest compression device. The monitoring device 106, in some cases, determines a parameter of the treatment by analyzing the signal detected by the sensor 108. This type of parameter, as described herein, can be referred to as a "treatment parameter." Examples of treatment parameters include timing, frequency, shape, or magnitude of the treatment.

In various implementations, the monitoring device 106 and the treating device 110 are communicatively coupled to one another. In particular examples, the monitoring device 106 or the treating device 110 reports a detected physiological parameter to the other device. For instance, the first treating device 110 may include a blood pressure sensor and may report a blood pressure of the patient 104 to the monitoring device 106. In some cases, the monitoring device 106 or the treating device 110 reports a treatment parameter to the other device. In some examples, the treating device 110 reports a frequency of chest compressions (and/or the start or stop times of the chest compressions) administered by the treating device 110 to the monitoring device 106. The receiving device may perform one or more actions based on the physiological parameter and/or the treatment parameter. Actions performed by the monitoring device 106 or the treating device 110 include initiating a measurement of a physiological parameter at a particular time or frequency, outputting a signal to the rescuer 102, outputting a signal to the patient 104, performing a treatment at a particular time or frequency, adjusting a treatment parameter of an ongoing treatment, or any combination thereof. According to some implementations, the monitoring device 106 or the treating device 110 instructs the other device to perform one or more actions. The receiving device, in turn, performs the action(s) based on the instruction from the monitoring device 106 or the first treating device 110. For instance, the monitoring device 106 instructs the treating device 110 to cease administering chest compressions to the patient 104 at a predetermined time, and the monitoring device 106 administers a defibrillation shock to the patient 104 at the particular time. By exchanging reports, instructions, or other data, the monitoring device 106 and the treating device 110 can coordinate monitoring and treatment of the patient 104.

To exchange data, the monitoring device 106 and/or the treating device 110 are configured to establish and/or communicate via a communication channel. As used herein, the term "communication channel," and its equivalents, may refer to a medium over which a first endpoint (e.g., a sender) transmits information to one or more second endpoints (e.g., receivers). Examples of communication channels include wired connections, such as Ethernet or fiber optic paths, as well as wireless connections, such as Institute of Electronics and Electrical Engineers (IEEE) (e.g., WI-FI, BLUETOOTH, etc.) or $3^{rd}$ Generation Partnership Program (3GPP) (e.g., Long Term Evolution (LTE), New Radio (NR), etc.) connections. As used herein, the term "endpoint," and its equivalents, may refer to an entity that is configured to transmit and/or receive data. Examples of endpoints include user equipment (UE) (e.g., mobile phones, tablet computers, etc.), computers, base stations, access points (APs), servers, compute nodes, medical devices, Internet of Things (IoT) devices, and the like.

In some implementations, the communication channel between the monitoring device 106 and the treating device 110 is established when the monitoring device 106 and the treating device 110 are paired. In particular cases, the monitoring device 106 and treating device 110 refrain from sharing substantive data (e.g., physiological metrics, reports about the patient 104, instructions for treating the patient 104, etc.) until the monitoring device 106 and the treating device 110 are paired. As used herein, the term "paired," and its equivalents, may refer to a state of multiple devices that have a shared link key that enables each device to cryptographically authenticate data it receives from any other device among the multiple devices.

In particular cases, a first paired device encrypts data prior to transmitting the data to a second paired device, and the second paired device restores the original data by decrypting the encrypted data. As used herein, the term "encrypt," and its equivalents, refers to a process of translating data from one format (e.g., an unencoded format) into an encoded format. In various cases, the encoded format is referred to as "ciphertext." Unencoded data, which has not been encrypted, may be referred to as being in "plaintext." In various examples, an entity encrypts data using at least one encryption key. An encryption key is a parameter that defines the translation of data from the one format into the encoded format. As used herein, the term "decrypt," and its equivalents, refers to a process of translating data from an encoded format into another format (e.g., an unencoded format), such as a plaintext format. In various examples, an entity encrypts data using at least one decryption key. A decryption key is a parameter that defines the translation of data from the encoded format into the other format. A link key, for example, is an encryption and/or decryption key.

Various cryptographic techniques can be utilized in accordance with the features described in this disclosure. For example, data can be encrypted and decrypted via a symmetric key, wherein the encryption key and the decryption key are equivalent. In some cases, data can be encrypted and decrypted via asymmetric keys, wherein the encryption key and the decryption key are different. Cryptographic hash functions (CHFs) are examples of cryptographic techniques. Examples of cryptographic techniques include the Data Encryption Standard (DES), Advanced Encryption Standard (AES), Elliptic Curve Cryptography (ECC), Rivest-Shamir-Adleman (RSA), Secure Hash Algorithm (SHA)-1, SHA-2, SHA-3, BLAKE, BLAKE2, BLAKE3, WHIRLPOOL, MD2, MD4, MD5, MD6, Temporal Key Integrity Protocol (TKIP), Rivest cipher 4 (RC4), variably modified permutation composition (VMPC), blowfish, Twofish, Threefish, Tiny Encryption Algorithm (TEA), Extended TEA (XTEA), Corrected Block TEA (XXTEA), Diffie-Hellman exchange (DHE), elliptic curve DHE, supersingular isogeny Diffie-Hellman (SIDH) key exchange, and so on. Any suitable encryption or decryption technique can be used in accordance with implementations of this disclosure.

In various implementations of the present disclosure, the monitoring device 106 generates unfiltered data 112 based on the physiological parameter detected by the sensor 108. For example, the monitoring device 106 includes an analog-to-digital converter (ADC) that converts a signal representing the physiological parameter into digital data. However, the patient 104 is simultaneously receiving a treatment from the treating device 110. In various cases, the treatment generates an artifact in the unfiltered data 112. For instance, the unfiltered data 112 represents an ECG of the patient 104 while the patient 104 is receiving chest compressions from the treating device 110, such that the unfiltered data 112 includes a chest compression artifact.

The artifact in the unfiltered data 112 may impede review of the physiological parameter by the rescuer 102 and/or the monitoring device 106. In some cases, the rescuer 102 is unable to identify whether the patient 104 is experiencing a dangerous medical condition due to the presence of the artifact. For example, the rescuer 102 may be unable to determine whether the patient 104 is experiencing an arrhythmia treatable by defibrillation (also referred to as a "shockable arrhythmia"), such as ventricular fibrillation (VF) or pulseless ventricular tachycardia (VT), due to the presence of the chest compression artifact in the unfiltered data 112 representing the ECG of the patient 104. While the rescuer 102 could temporarily pause the chest compressions by operating the treating device 110, and view the unfiltered data 112 without the chest compression artifact, such a pause in chest compressions could harm the patient 104. Thus, it is preferred to avoid pauses in chest compressions and other treatments during rescue events.

In various implementations of the present disclosure, the monitoring device 106 is configured to generate filtered data 114 by at least partially removing the artifact from the unfiltered data 112. In some examples, the monitoring device 106 applies a filter to the unfiltered data 112, such as an adaptive filter (e.g., a Wiener filter, a Kalman filter, or the like), an nth order filter (e.g., a zero-th order filter) a comb filter, an inverse comb filter, a high-pass filter, a band reject filter, a finite impulse response (FIR) filter, an infinite impulse response (IIR) filter, or a combination thereof. In some cases, the monitoring device 106 converts the unfiltered data 112 from the time domain into the frequency (e.g., a Fourier) domain, a Laplace domain, a Z-transform domain, or a wavelet (e.g., a continuous wavelet transform, a discrete wavelet transform, etc.) domain, and removes at least a portion of the artifact by processing the converted data. According to some examples, the monitoring device 106 identifies and subtracts the artifact from the unfiltered data 112. In some instances, the monitoring device 106 identifies and subtracts the artifact based on the detected treatment. For example, the monitoring device 106 detects another signal indicative of the treatment, such as compression data from a chest compression sensor, cross-correlates the unfiltered data 112 with the data corresponding to the treatment (e.g., the impedance, the acceleration of a separate compression detector, the velocity of the compression detector, etc.), identifies the artifact based on the cross-correlation, and subtracts the artifact from the unfiltered data 112. In some instances, the monitoring device 106 denoises the unfiltered data 112. For example, the monitoring device 106 removes at least a portion of the artifact by performing spectral subtraction on the unfiltered data 112.

In some implementations, the artifact removal and/or filtering technique applied by the monitoring device 106 is associated with a latency period. As used herein, the term "latency period" refers to an interval between a time at which a filter is initially applied to unfiltered data and a time at which an artifact is substantially removed from the unfiltered data by the filter. Several factors contribute to the latency period of a filter. Adaptive filters, for instance, are associated with a greater latency period than non-adaptive filters, because they may be configured to learn the artifact during the latency period. Artifact removal and/or filtering techniques that require conversion to a separate domain, such as the Fourier domain, may also be associated with a longer latency period than alternative techniques. Various types of digital filters are associated with different types of non-zero latency periods.

Optionally, the monitoring device 106 applies additional filtering techniques to reduce the harmonics of the artifact in the selected segment of the unfiltered data 112. In particular cases, the monitoring device 106 generates the filtered data 114 by applying a comb filter or multiple notch filters to the unfiltered data 112. In various instances, comb filters are particularly suited to remove chest compression artifacts administered by a mechanical chest compression device. In some cases, an example comb filter rejects a band including the frequency of the chest compressions as well as one or more harmonics of the frequency. For example, the monitoring device 106 applies a comb filter with multiple stopbands that correspond to the fundamental frequency of the treatment administered to the patient 104 and one or more harmonics of the fundamental frequency. In some implementations, the treating device 110 reports the frequency of the chest compressions to the monitoring device 106 over the communication channel, and the monitoring device 106 generates and/or adjusts the filter applied to the unfiltered data 112 accordingly. In some implementations, the monitoring device 106 identifies the frequency of the chest compressions by analyzing the unfiltered data 112 itself.

In some cases, the filtered data 114 more accurately reflects the condition of the patient 104 than the unfiltered data 112. However, this is not always the case. In some examples, the unfiltered data 112 is more helpful for analysis by the monitoring device 106 and/or for display to the rescuer 102 than the filtered data 114.

In various implementations, the monitoring device 106 selectively displays the filtered data 114 to the rescuer 102 when one or more conditions (also referred to as "preconditions") are met. For example, the monitoring device 106 refrains from displaying the filtered data 114 unless the filtered data 114 is more reliable than the unfiltered data 112. As used herein, the term "reliable," and its equivalents, can refer to data that accurately represents a condition of a patient.

In some cases, the monitoring device 106 determines whether the treating device 110 is administering the treatment, and selectively outputs (e.g., displays) the filtered data 114 when the treating device 110 is administering the treatment. For instance, if the treating device 110 temporarily pauses administering the treatment to the patient 104, but the monitoring device 106 continues to apply the filter to the unfiltered data 112, then the filtered data 114 will be noisier and/or less representative of the condition of the patient 104 than the unfiltered data 112. In some examples in which the treating device 110 alters the treatment administered to the patient 104 (e.g., the treating device 110 changes a frequency of ventilations administered to the patient 104), but the monitoring device 106 continues to apply the filter optimized to the original treatment parameter, then the filtered data 114 will be noisier and/or less representative of the condition of the patient 104 than the unfiltered data 112.

The monitoring device 106 prevents output of the filtered data 114 in response to determining that the treating device 110 is not administering the treatment. For example, the monitoring device 106 determines that the treating device 110 is not administering the treatment by determining that an artifact associated with the treatment is absent from the unfiltered data 112. In some cases, the monitoring device 106 determines that the treating device 110 is not administering the treatment by receiving a communication signal from the treating device 110, which indicates that the treating device 110 is not administering the treatment.

In some cases, the monitoring device 106 prevents output of the filtered data 114 in response to determining that the treatment has been altered. For instance, the monitoring device 106 determines that the treatment is administered at a different frequency and/or phase by analyzing the unfiltered data 112. In some cases, the treating device 110 transmits a communication signal to the monitoring device 106 that indicates the alteration in the treatment. In some cases (e.g., in which the monitoring device 106 applies an adaptive filter), the change in the treatment may cause a latency period in which the monitoring device 106 relearns the artifact that has been altered by the changed treatment. In some implementations, the monitoring device 106 prevents output of the filtered data 114 during the latency period of the filter applied by the monitoring device 106.

In some cases, the monitoring device 106 prevents output of the filtered data 114 upon detecting that the sensor 108 has been disconnected from the patient 104.

According to some examples, the monitoring device 106 prevents output of the filtered data 114 when the monitoring device 106 is communicatively disconnected from the treating device 110. For example, the monitoring device 106 is wirelessly paired with the treating device 110, and exchanges communication signals with the treating device 110 (e.g., periodically). However, if the monitoring device 106 determines that it has not received an expected communication signal from the treating device 110, then the monitoring device may determine that the monitoring device 106 is no longer paired with the treating device 110. In some cases, the monitoring device 106 receives an unpairing request from the treating device 110. In various implementations, the monitoring device 106 exclusively outputs the unfiltered data 112 when the monitoring device 106 determines that it is no longer paired with the treating device 110.

In some implementations, the monitoring device 106 prevents output of the filtered data 114 upon detecting a non-treatment artifact in the unfiltered data 112. For instance, the monitoring device 106 prevents output of the filtered data 114 upon detecting a rail artifact (e.g., the unfiltered data 112 is saturated and/or its amplitude exceeds an upper limit of the sensor 108) in the unfiltered data 112. The monitoring device 106, in some cases, prevents output of the filtered data 114 upon detecting a motion artifact in the unfiltered data 112 (e.g., indicating that the patient 104 has moved).

In some examples, the monitoring device 106 includes an accelerometer that determines whether the monitoring device 106 is moving. In some cases, the filter applied by the monitoring device 106 loses efficacy if there is a motion artifact introduced into the unfiltered data 112 due to motion of the monitoring device 106. In some cases, the accelerometer is coupled to the patient 104. For instance, the accelerometer is configured to detect movement of the chest of the patient 104, thereby detecting chest compressions administered to the patient 104 or some other type of motion artifact. In some cases, the accelerometer is coupled to a portion of the patient 104 that is not receiving the treatment to the patient 104, such as a foot of the patient 104. In some cases, the accelerometer is coupled to a cot or other surface on which the patient 104 is disposed. The accelerometer, for instance, detects whether the patient 104 is moving (e.g., such as after regaining consciousness). In various cases, the movement of the patient 104 introduces the motion artifact. Accordingly, in various implementations, the monitoring device 106 prevents output of the unfiltered data 112 when an acceleration of the monitoring device 106 is above a threshold, or when the monitoring device 106 has detected an acceleration that is above the threshold within a predetermined time period (e.g., the last one minute).

In some cases, the treating device 110 administers a first treatment to the patient 104, and a second treatment is also administered to the patient 104 (e.g., by the treating device 110, another treating device, or the rescuer 102). For instance, the treating device 110 administers chest compressions to the patient 104, and the rescuer 102 may intubate the patient 104 using an intubation tube and/or ventilation device. The monitoring device 106, for instance, is configured to remove the artifact caused by the first treatment to the patient 104, but is not configured to remove an artifact caused by the second treatment to the patient 104. Accordingly, the monitoring device 106 may prevent output of the filtered data 114 upon detecting that the second treatment is being administered to the patient 104. In some cases, the monitoring device 106 detects that the second treatment is being administered to the patient 104 by analyzing the unfiltered data 112 (e.g., detecting the artifact caused by the second treatment in the unfiltered data 112). In some examples, the monitoring device 106 detects that the second treatment is being administered to the patient 104 by receiving a communication signal from the device administering the second treatment, wherein the communication signal indicates the second treatment.

According to various implementations of the present disclosure, the monitoring device 106 simultaneously displays the unfiltered data 112 and the filtered data 114 to the rescuer 102 when one or more of the conditions have been satisfied. For example, a display of the monitoring device 106 visually presents a first waveform representing the unfiltered data 112 and a second waveform representing the filtered data 114. In some examples, the first waveform overlaps and/or time-aligned with the second waveform. Accordingly, the rescuer 102 can manually observe the unfiltered data 112 and the filtered data 114 at the same time. In cases where the unfiltered data 112 or the filtered data 114 is less reliable than the other type of data, the rescuer 102 may manually review the more reliable type of data in order to accurately assess the condition of the patient 104.

In some cases, the monitoring device 106 emphasizes one type of data over another type of data visually presented on the display. For instance, the monitoring device 106 emphasizes a first waveform representing the unfiltered data 112 differently than a second waveform representing the filtered data 114. The waveforms, for instance, have different colors, transparencies, line styles (e.g., dashed, dotted, or solid line styles), boldness, contrast, widths, blinking patterns, or any combination thereof. In some cases, one waveform has a greater emphasis than the other waveform when it is displayed with a predetermined color, a lower transparency, a predetermined line style (e.g., a solid line style), a greater boldness, a greater contrast, a larger width, without blinking, or any combination thereof. In various implementations, he monitoring device 106 displays the filtered data 114 at the greater emphasis, as illustrated in FIG. 1. In some implementations, the monitoring device 106 displays the filtered data 114 without displaying the unfiltered data 112.

In various cases, the monitoring device 106 selectively outputs the filtered data 114 when the condition(s) are satisfied and the monitoring device 106 has received an input signal from the rescuer 102. The monitoring device 106 includes a selection element 116, which the monitoring device 106 utilizes to detect the input signal. The selection element 116 is a button, at least one touch sensor, or any other type of input device. In some implementations, upon detecting that the condition(s) are satisfied, the monitoring device 106 outputs a notification indicating that filtering is available. For instance, the notification is displayed on a touchscreen of the monitoring device 106, and the monitoring device 106 detects the input signal by detecting a touch of the rescuer 102 on one or more touch sensors overlapping the notification on the touchscreen. In some cases, the notification is a toggle switch or drop-down menu. Accordingly, the monitoring device 106 outputs a selectable option to display the filtered data 114 in response to determining that the condition(s) are satisfied. In various cases, the monitoring device 106 refrains from outputting the filtered data 114 unless the input signal is detected.

According to some implementations, the monitoring device 106 generates the filtered data 114 regardless of whether the filtered data 114 is output by the monitoring device 106. For instance, the monitoring device 106 generates the filtered data 114 using a background process before the monitoring device 106 detects the input signal. Accordingly, in cases wherein the filter applied by the monitoring device 106 is associated with a latency period, the monitoring device 106 can output the filtered data 114 immediately upon detecting the input signal, without waiting for the latency period to elapse.

Figures 2A, 2B, 2C:
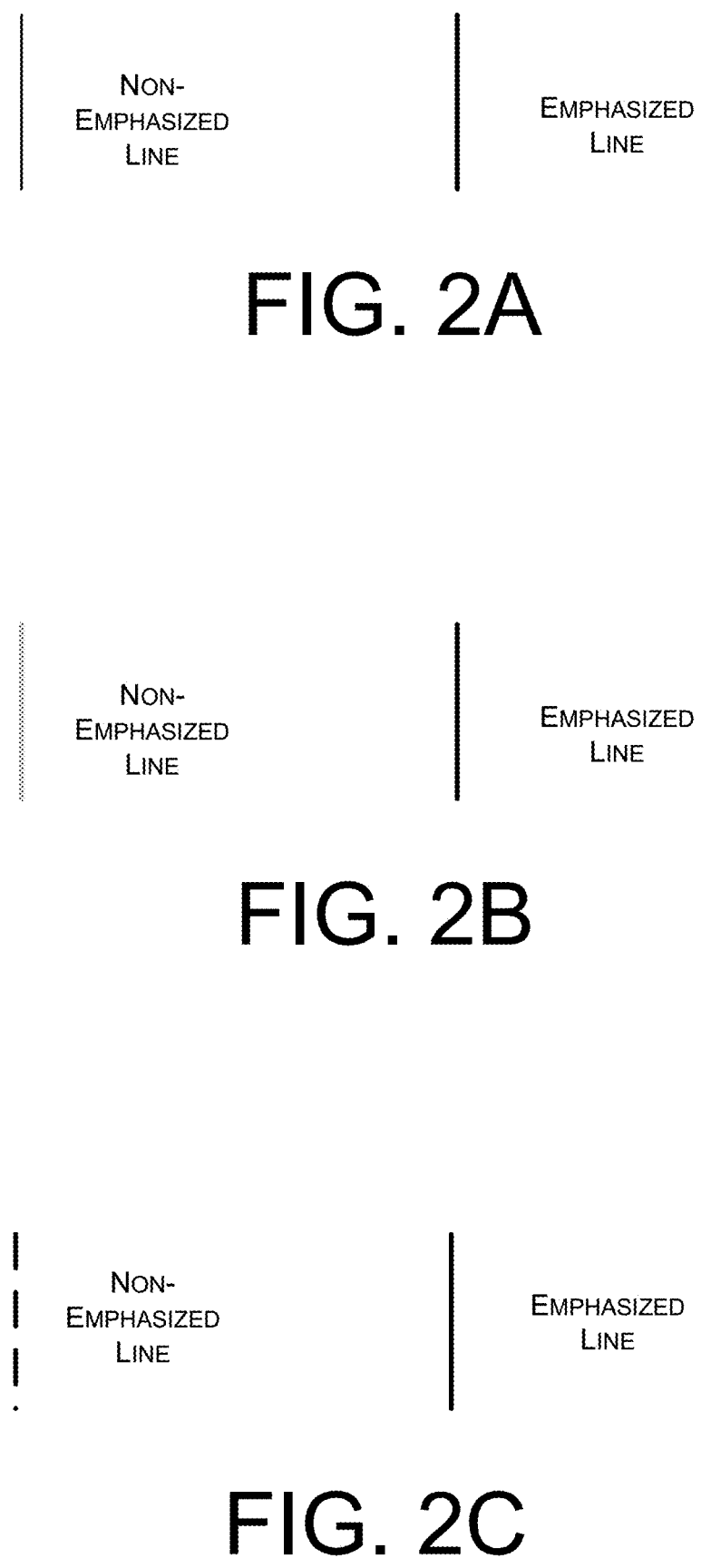

FIGS. 2A to 2C illustrate different examples of emphasized lines. In various implementations, a medical device (e.g., the monitoring device 106) displays multiple waveforms simultaneously, such as waveforms representing filtered and unfiltered data. To distinguish between the waveforms, the medical device displays the lines of the waveforms at different emphasis.

FIG. 2A illustrates a non-emphasized line 202 and an emphasized line 204 having different widths. In particular, the non-emphasized line 202 has a shorter width than the emphasized line 204.

FIG. 2B illustrates an non-emphasized line 206 and an emphasized line 208 having different colors, contrast, or transparencies. The non-emphasized line 206 has a different color than the emphasized line. For instance, the emphasized line 208 has a bolder, more pigmented color than the non-emphasized line 206. In some cases, the non-emphasized line 206 has a lower contrast with respect to a background than the emphasized line 208. In various examples, the non-emphasized line 206 has a greater transparency than the emphasized line 208.

FIG. 2C illustrates a non-emphasized line 210 and an emphasized line 212 having different line styles. In particular, the non-emphasized line 210 has a dashed line style, whereas the emphasized line has a solid line style.

Figure 3:
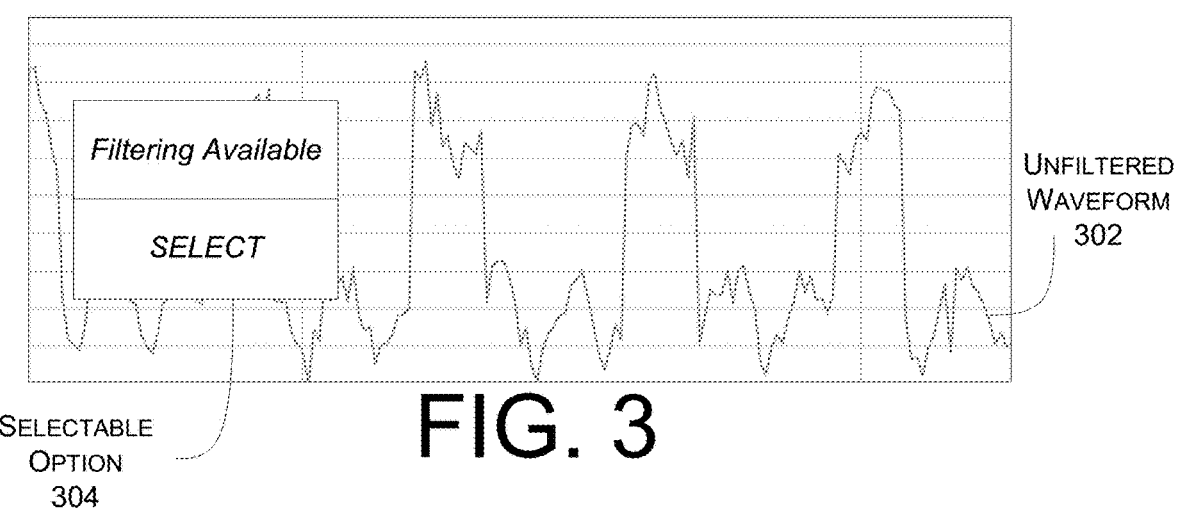
FIG. 3 illustrates an example display of a medical device that performs selective filtering.

FIG. 3 illustrates an example display 300 of a medical device that performs selective filtering. In particular, the display 300 visually presents an unfiltered waveform 302 representing a signal detected from an individual, such as a patient. In various implementations, the signal is indicative of a physiological parameter of the individual. However, the unfiltered waveform 302 further includes an artifact, such as an artifact caused by a treatment being performed on the individual. In the example of FIG. 3, the unfiltered waveform 302 is representative of an ECG of an individual as well as an artifact caused by chest compressions administered to the individual. Due to the presence of the chest compression artifact, it is difficult for a user to manually discern whether the individual is experiencing some sort of arrhythmia.

In various cases, the medical device determines that one or more conditions have been satisfied. For instance, the medical device determines that the treatment is being administered to the individual. In some cases, the medical device determines that an acceleration of the medical device is below a threshold acceleration. In some examples, the medical device determines that the acceleration of the medical device has been below the threshold acceleration for greater than a threshold time period. In various instances, the medical device determines that another treatment is not currently being performed on the individual.

Upon determining that the condition(s) are satisfied, the medical device outputs a selectable option 304 on the display 300. The selectable option 304 is a user interface element that indicates filtering is available. For instance, the medical device is generating filtered data using a background process on the data representing the unfiltered waveform 302. However, the medical device may refrain from outputting the filtered data until the user selects the selectable option 304. In some cases, the display 300 is integrated with one or more touch sensors. For instance, the display 300 is a touchscreen. The medical device, in some cases, outputs the filtered data upon detecting that the user has touched the selectable option 304.

Figure 4:
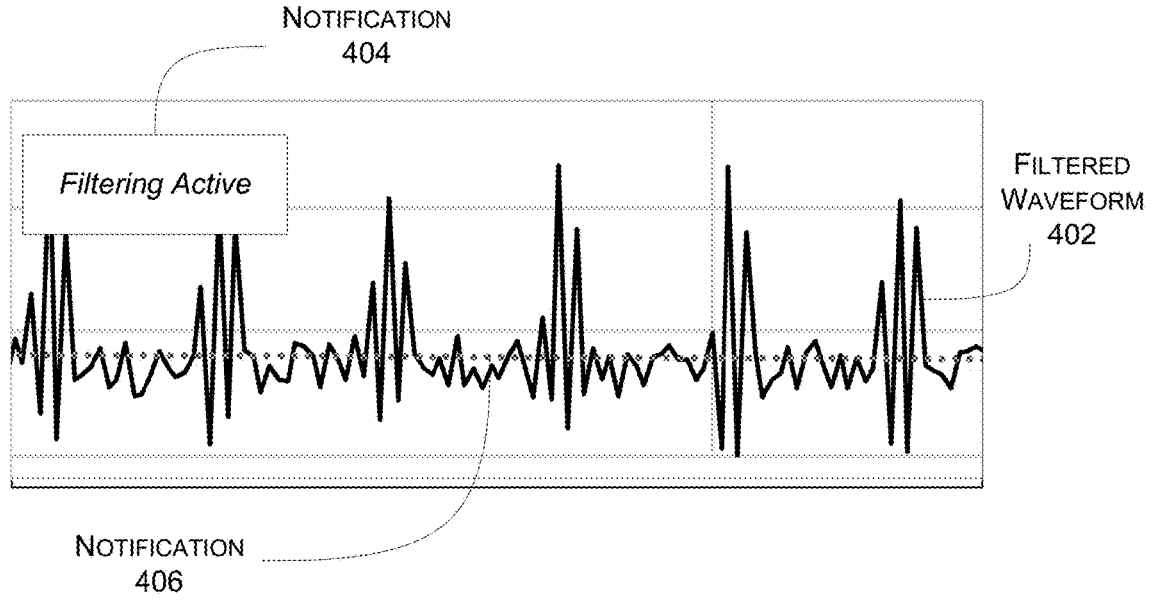
FIG. 4 illustrates an example display of a medical device that outputs filtered data.

FIG. 4 illustrates an example display 400 of a medical device that outputs filtered data. For example, the medical device may detect that one or more conditions have been satisfied. In some cases, the medical device also detects an input signal from a user, wherein the input signal selects filtering. For example, the medical device enabled a selectable option upon detecting that the condition(s) have been satisfied, and detected that the user has selected the selectable option.

The display 400 outputs a filtered waveform 402 corresponding to the filtered data. In various implementations, the filtered waveform 402 is representative of data indicating a physiological parameter of an individual, wherein an artifact has additionally been removed. The artifact, for example, corresponds to a treatment administered to the individual. For example, the medical device detected a signal indicative of an ECG of the individual while the individual was receiving chest compressions. In various cases, the medical device generated the filtered waveform 402 by removing, from data representing the signal, an artifact associated with the chest compressions. In some implementations, the display 400 further outputs a notification 404. The notification 404 is a user interface element indicating that the filtered waveform 402 is filtered, and not representative of the raw signal detected by the medical device.

In some implementations, the display 400 includes another type of notification 406 that indicates that the display 400 is currently outputting the filtered waveform 402. In FIG. 4, the notification includes a dashed line overlapping the filtered waveform 402, but implementations are not so limited. In some cases, the display 400 outputs the filtered waveform 402 in a particular color (e.g., a different color than the unfiltered waveform 302), or outputs another type of symbol as the notification 406. Accordingly, a user may readily identify that the display 400 is outputting the filtered waveform 402 rather than the unfiltered waveform 302.

Although not specifically illustrated in FIG. 4, the display 400 may output an unfiltered waveform (e.g., the unfiltered waveform 302) and the filtered waveform 402 simultaneously. For example, the unfiltered waveform and the filtered waveform 402 may be overlapping and/or time-aligned on the display 400. In some implementations, the filtered waveform 402 is displayed at a greater emphasis than the unfiltered waveform on the display 400.

In some implementations, the user may cause the display 400 to output the unfiltered waveform 302, even when filtering is active. For instance, the display 400 may present another selectable option (not illustrated) that, when selected by the user, causes the display to output the unfiltered waveform 302. Thus, the user may selectively disable display of the filtered waveform 402.

Figure 5:
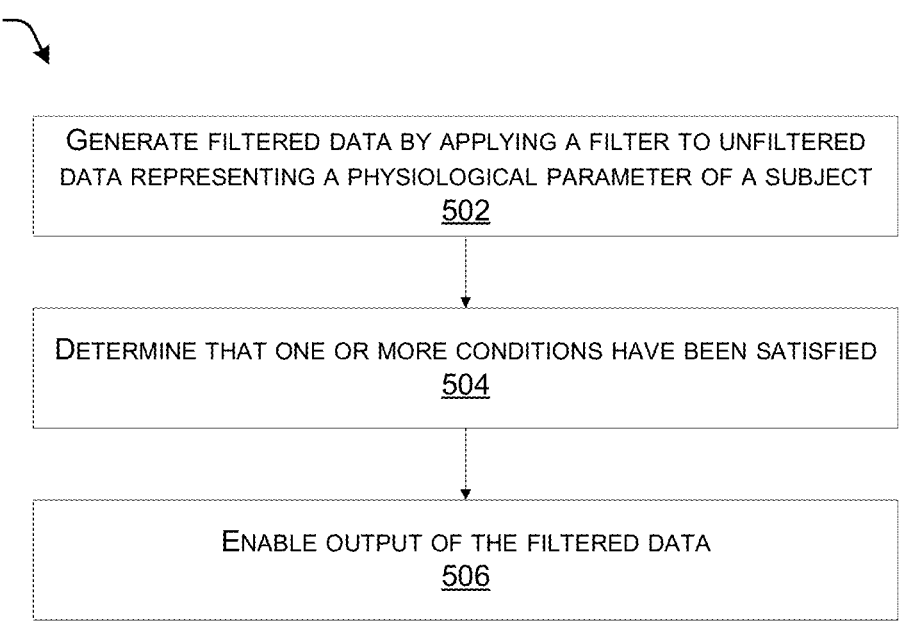
FIG. 5 illustrates an example process for selectively outputting filtered data.

FIG. 5 illustrates an example process 500 for selectively outputting filtered data. The process 500 is performed by an entity, such as a medical device, the monitoring device 106, a processor executing instructions stored in memory, or any combination thereof.

At 502, the entity generates filtered data by applying a filter to unfiltered data representing a physiological parameter of a subject. In various implementations, the physiological parameter includes an electrocardiogram (ECG), a capnograph, a transthoracic impedance, a force administered to a user, a blood pressure, an airway parameter, a partial pressure of oxygen, an electroencephalogram (EEG), a temperature, a blood flow, or a pulse rate of the subject. In some cases, the entity includes a sensor that generates an analog signal based on the physiological parameter. The entity may convert the analog signal to digital data, in order to generate the unfiltered data. In some cases, the entity receives the unfiltered data from a separate device that includes the sensor.

The unfiltered data may include an artifact. For example, the artifact is caused by a treatment being administered to the subject. In various cases, the artifact is a chest compression artifact, a ventilation artifact, or the like. The filter may be configured to remove at least a portion of the artifact. In some implementations, the filter is a comb filter that includes a band rejecting the frequency of the treatment as well as one or more harmonics of the frequency. In some implementations, the entity generates the filter based on a communication signal from a medical device administering the treatment to the subject. For instance, a mechanical chest compression device reports the frequency at which it is administering chest compressions to the entity.

At 504, the entity determines that one or more conditions have been satisfied. For example, the entity determines that the medical device is administering the treatment to the subject. In some cases, the entity determines that a latency period of the filter has expired. In various examples, the entity determines that the medical device has not changed the treatment within a threshold time period. According to some implementations, the entity determines that the device generating the unfiltered data (e.g., the entity or a separate device) has not moved greater than a threshold acceleration and/or has not moved greater than the threshold acceleration within a predetermined time period. In some cases, the entity determines that another treatment is not being administered to the subject.

At 506, the entity enables output of the filtered data. In some implementations, the entity outputs the filtered data with the unfiltered data. For instance, the entity displays a waveform representing the filtered data and a waveform representing the unfiltered data, simultaneously on a display. In some cases, the entity emphasizes the waveform representing the filtered data over the waveform representing the unfiltered data. For example, the waveforms have different colors, different contrasts, different line sizes, different transparencies, or different line styles. In various implementations, the entity outputs the filtered data without the unfiltered data. The entity, for instance, may further output a notification indicating that the data has been filtered.

In some cases, the entity enables output of the filtered data in response to detecting an input signal from a user. For instance, in response to determining that the condition(s) have been satisfied at 504, the entity outputs a selectable option for filtering. Upon detecting that the selectable option has been selected by the user, the entity outputs the filtered data.

In various implementations, the entity additionally checks whether the condition(s) have been satisfied after the entity enables output of the filtered data at 506. For instance, the entity checks the condition(s) periodically (e.g., every second, every ten seconds, etc.). If the entity determines that the condition(s) have no longer been satisfied, the entity prevents further output of the filtered data.

Figure 6:
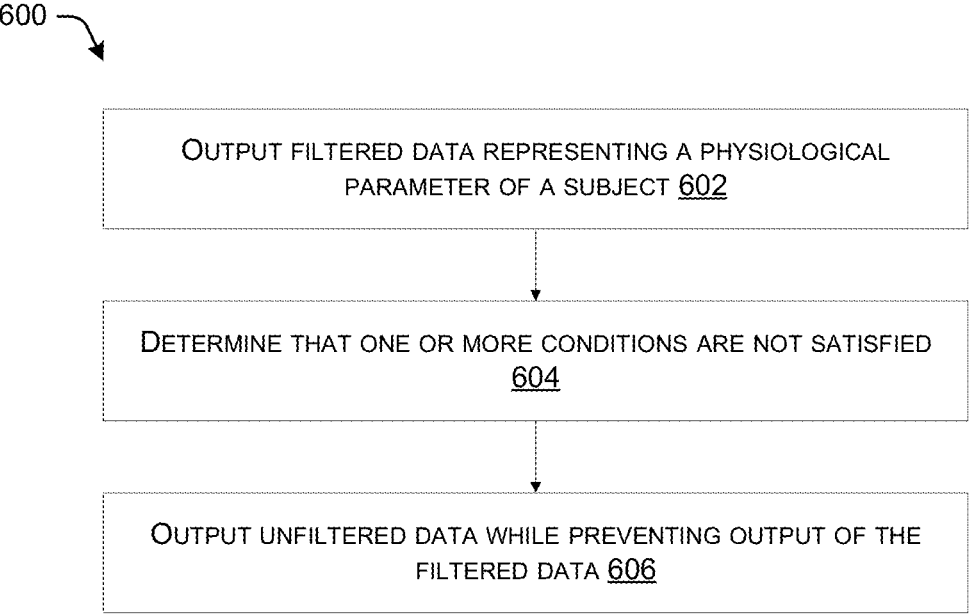
FIG. 6 illustrates an example process for refraining from outputting filtered data.

FIG. 6 illustrates an example process 600 for refraining from outputting filtered data. The process 600 is performed by an entity, such as a medical device, the monitoring device 106, a processor executing instructions stored in memory, or any combination thereof.

At 602, the entity outputs filtered data representing a physiological parameter of a subject. For instance, the entity generates the filtered data by applying a filter to unfiltered data representing the physiological parameter. In various implementations, the physiological parameter includes an electrocardiogram (ECG), a capnograph, a transthoracic impedance, a force administered to a user, a blood pressure, an airway parameter, a partial pressure of oxygen, an electroencephalogram (EEG), a temperature, a blood flow, or a pulse rate of the subject. In some cases, the entity includes a sensor that generates an analog signal based on the physiological parameter. The entity may convert the analog signal to digital data, in order to generate the unfiltered data. In some cases, the entity receives the unfiltered data from a separate device that includes the sensor.

The unfiltered data may include an artifact. For example, the artifact is caused by a treatment being administered to the subject. In various cases, the artifact is a chest compression artifact, a ventilation artifact, or the like. The filter may be configured to remove at least a portion of the artifact. In some implementations, the filter is a comb filter that includes a band rejecting the frequency of the treatment as well as one or more harmonics of the frequency. In some implementations, the entity generates the filter based on a communication signal from a medical device administering the treatment to the subject. For instance, a mechanical chest compression device reports the frequency at which it is administering chest compressions to the entity.

In various implementations, the entity outputs a waveform representing the filtered data. According to some examples, the entity visually presents the waveform representing the filtered data and a waveform representing the unfiltered data simultaneously. For example, the waveforms are time-aligned and overlapping on a display. In various cases, the waveform representing the filtered data is presented at a greater emphasis than the waveform representing the unfiltered data. For example, the waveforms have different colors, different contrasts, different line sizes, different transparencies, or different line styles.

At 604, the entity determines that one or more conditions are not satisfied. For example, the entity determines that the medical device is not administering the treatment to the subject. In some cases, the entity determines that a latency period of the filter is currently occurring. In various examples, the entity determines that the medical device has changed the treatment within a threshold time period. According to some implementations, the entity determines that the device generating the unfiltered data (e.g., the entity or a separate device) has moved greater than a threshold acceleration and/or has moved greater than the threshold acceleration within a predetermined time period. In some cases, the entity determines that another treatment is being administered to the subject. In some cases, the entity determines that at least one condition among a group of conditions is unsatisfied.

At 606, the entity outputs unfiltered data while preventing output of the filtered data. For example, the entity outputs the waveform representing the unfiltered data without outputting the waveform representing the filtered data.

Figure 7:
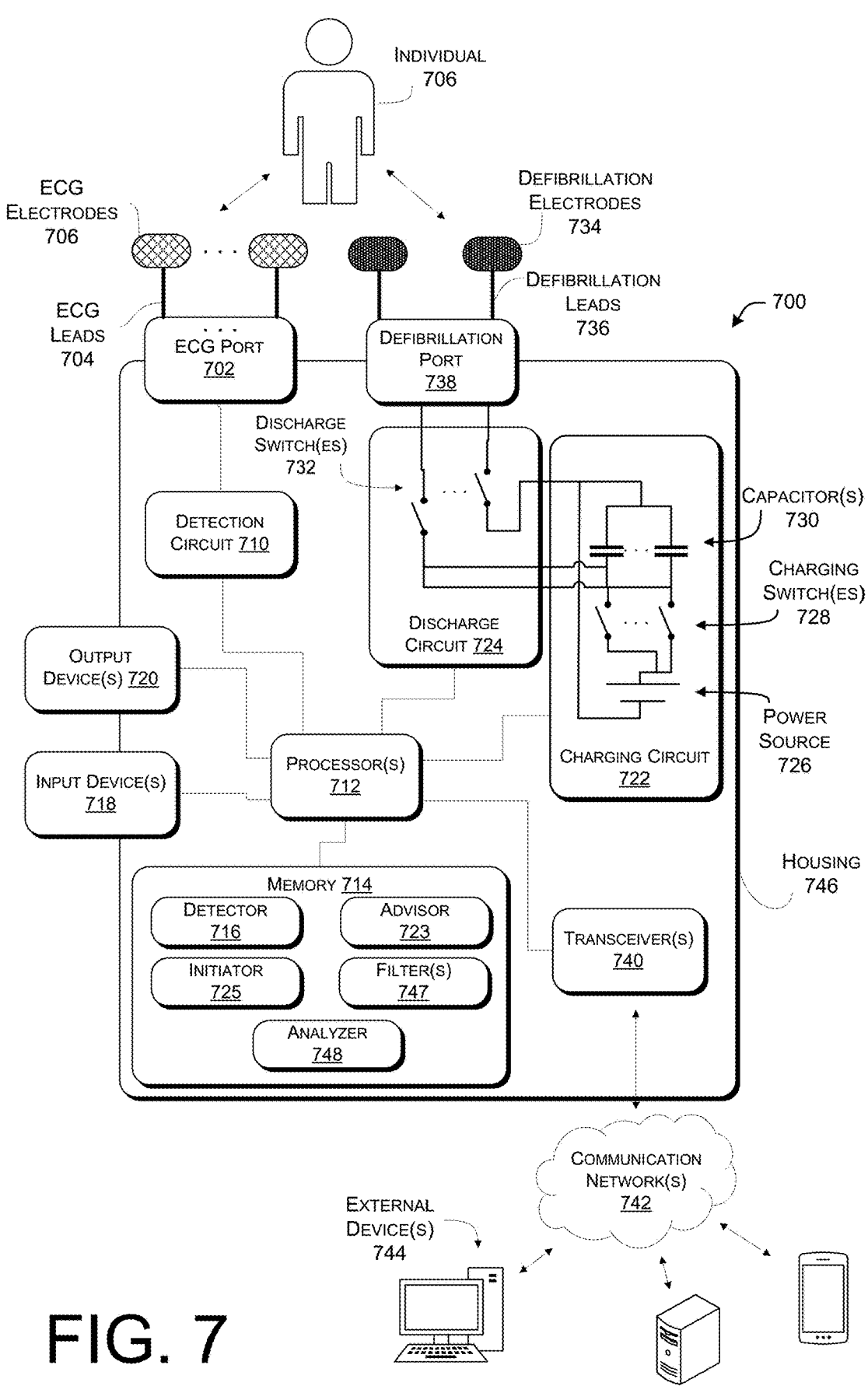
FIG. 7 illustrates an example of an external defibrillator configured to perform various functions described herein.

FIG. 7 illustrates an example of an external defibrillator 700 configured to perform various functions described herein. For example, the external defibrillator 700 is the monitoring device 106 or the treating device 110 described above with reference to FIG. 1.

The external defibrillator 700 includes an electrocardiogram (ECG) port 702 connected to multiple ECG leads 704. In some cases, the ECG leads 704 are removeable from the ECG port 702. For instance, the ECG leads 704 are plugged into the ECG port 702. The ECG leads 704 are connected to ECG electrodes 706, respectively. In various implementations, the ECG electrodes 706 are disposed on different locations on an individual 708. A detection circuit 710 is configured to detect relative voltages between the ECG electrodes 706. These voltages are indicative of the electrical activity of the heart of the individual 708.

In various implementations, the ECG electrodes 706 are in contact with the different locations on the skin of the individual 708. In some examples, a first one of the ECG electrodes 706 is placed on the skin between the heart and right arm of the individual 708, a second one of the ECG electrodes 706 is placed on the skin between the heart and left arm of the individual 708, and a third one of the ECG electrodes 706 is placed on the skin between the heart and a leg (either the left leg or the right leg) of the individual 708. In these examples, the detection circuit 710 is configured to measure the relative voltages between the first, second, and third ECG electrodes 706. Respective pairings of the ECG electrodes 706 are referred to as "leads," and the voltages between the pairs of ECG electrodes 706 are known as "lead voltages." In some examples, more than three ECG electrodes 706 are included, such that 5-lead or 12-lead ECG signals are detected by the detection circuit 710.

The detection circuit 710 includes at least one analog circuit, at least one digital circuit, or a combination thereof. The detection circuit 710 receives the analog electrical signals from the ECG electrodes 706, via the ECG port 702 and the ECG leads 704. In some cases, the detection circuit 710 includes one or more analog filters configured to filter noise and/or artifact from the electrical signals. The detection circuit 710 includes an analog-to-digital (ADC) in various examples. The detection circuit 710 generates a digital signal indicative of the analog electrical signals from the ECG electrodes 706. This digital signal can be referred to as an "ECG signal" or an "ECG."

In some cases, the detection circuit 710 further detects an electrical impedance between at least one pair of the ECG electrodes 706. For example, the detection circuit 710 includes, or otherwise controls, a power source that applies a known voltage (or current) across a pair of the ECG electrodes 706 and detects a resultant current (or voltage) between the pair of the ECG electrodes 706. The impedance is generated based on the applied signal (voltage or current) and the resultant signal (current or voltage). In various cases, the impedance corresponds to respiration of the individual 708, chest compressions performed on the individual 708, and other physiological states of the individual 708. In various examples, the detection circuit 710 includes one or more analog filters configured to filter noise and/or artifact from the resultant signal. The detection circuit 710 generates a digital signal indicative of the impedance using an ADC. This digital signal can be referred to as an "impedance signal" or an "impedance." In some cases, the detection circuit 710 includes additional components configured to detect electrical signals representing other types of physiological parameters described herein. One or more ADCs in the detection circuit 710 are further configured to convert the detected electrical signals into digital data.

The detection circuit 710 provides the ECG signal, the impedance signal, and/or signals representing other physiological parameters to one or more processors 712 in the external defibrillator 700. In some implementations, the processor(s) 712 includes a central processing unit (CPU), a graphics processing unit (GPU), both CPU and GPU, or other processing unit or component known in the art.

The processor(s) 712 is operably connected to memory 714. In various implementations, the memory 714 is volatile (such as random access memory (RAM)), non-volatile (such as read only memory (ROM), flash memory, etc.) or some combination of the two. The memory 714 stores instructions that, when executed by the processor(s) 712, causes the processor(s) 712 to perform various operations. In various examples, the memory 714 stores methods, threads, processes, applications, objects, modules, any other sort of executable instruction, or a combination thereof. In some cases, the memory 714 stores files, databases, or a combination thereof. In some examples, the memory 714 includes, but is not limited to, RAM, ROM, electrically erasable programmable read-only memory (EEPROM), flash memory, or any other memory technology. In some examples, the memory 714 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 712 and/or the external defibrillator 700. In some cases, the memory 714 at least temporarily stores the ECG signal and/or the impedance signal.

In various examples, the memory 714 includes a detector 716, which causes the processor(s) 712 to determine, based on the ECG signal and/or the impedance signal, whether the individual 708 is exhibiting a particular heart rhythm. For instance, the processor(s) 712 determines whether the individual 708 is experiencing a shockable rhythm that is treatable by defibrillation. Examples of shockable rhythms include VF and pulseless VT. In some examples, the processor(s) 712 determines whether any of a variety of different rhythms (e.g., asystole, sinus rhythm, atrial fibrillation (AF), etc.) are present in the ECG signal. In various implementations, the detector 716, when executed by the processor(s) 712, further causes the processor(s) 712 to identify one or more physiological events in data representing various physiological parameters described herein.

The processor(s) 712 is operably connected to one or more input devices 718 and one or more output devices 720. Collectively, the input device(s) 718 and the output device(s) 720 function as an interface between a user and the defibrillator 700. The input device(s) 718 is configured to receive an input from a user and includes at least one of a keypad, a cursor control, a touch-sensitive display, a voice input device (e.g., a microphone), a haptic feedback device (e.g., a gyroscope), an accelerometer, or any combination thereof. The output device(s) 720 includes at least one of a display, a speaker, a haptic output device, a printer, or any combination thereof. In various examples, the processor(s) 712 causes a display among the input device(s) 718 to visually output a waveform of the ECG signal and/or the impedance signal. In some implementations, the input device(s) 718 includes one or more touch sensors, the output device(s) 720 includes a display screen, and the touch sensor(s) are integrated with the display screen. Thus, in some cases, the external defibrillator 700 includes a touch-screen configured to receive user input signal(s) and visually output physiological parameters, such as the ECG signal and/or the impedance signal.

In some examples, the memory 714 includes an advisor 723, which, when executed by the processor(s) 712, causes the processor(s) 712 to generate advice and/or control the output device(s) 720 to output the advice to a user (e.g., a rescuer). In some examples, the processor(s) 712 provides, or causes the output device(s) 720 to provide, an instruction to perform CPR on the individual 708. In some cases, the processor(s) 712 evaluates, based on the ECG signal, the impedance signal, or other physiological parameters, CPR being performed on the individual 708 and causes the output device(s) 720 to provide feedback about the CPR in the instruction. According to some examples, the processor(s) 712, upon identifying that a shockable rhythm is present in the ECG signal, causes the output device(s) 720 to output an instruction and/or recommendation to administer a defibrillation shock to the individual 708.

The memory 714 also includes an initiator 725 which, when executed by the processor(s) 712, causes the processor(s) 712 to control other elements of the external defibrillator 700 in order to administer a defibrillation shock to the individual 708. In some examples, the processor(s) 712 executing the initiator 725 selectively causes the administration of the defibrillation shock based on determining that the individual 708 is exhibiting the shockable rhythm and/or based on an input from a user (received, e.g., by the input device(s) 718. In some cases, the processor(s) 712 causes the defibrillation shock to be output at a particular time, which is determined by the processor(s) 712 based on the ECG signal and/or the impedance signal.

In various implementations, the memory 714 further include one or more filters 747 which, when executed by the processor(s) 712, cause the processor(s) 712 to filter and/or remove artifact from one or more sets of data generated by the detection circuit 710. Further, the memory 714 stores an emphasizer 748 which, when executed by the processor(s) 712, cause the processor(s) 712 to cause a display in the output device(s) 720 to display one or more waveforms, symbols, and other visual signals described herein. The emphasizer 748 further causes the processor(s) 712 to determine whether to output one type of data (e.g., filtered data) and/or another type of data (e.g., unfiltered data), and causes the display to emphasize one set of data over another on the display.

The processor(s) 712 is operably connected to a charging circuit 722 and a discharge circuit 724. In various implementations, the charging circuit 722 includes a power source 726, one or more charging switches 728, and one or more capacitors 730. The power source 726 includes, for instance, a battery. The processor(s) 712 initiates a defibrillation shock by causing the power source 726 to charge at least one capacitor among the capacitor(s) 730. For example, the processor(s) 712 activates at least one of the charging switch(es) 728 in the charging circuit 722 to complete a first circuit connecting the power source 726 and the capacitor to be charged. Then, the processor(s) 712 causes the discharge circuit 724 to discharge energy stored in the charged capacitor across a pair of defibrillation electrodes 730, which are in contact with the individual 708. For example, the processor(s) 712 deactivates the charging switch(es) 728 completing the first circuit between the capacitor(s) 730 and the power source 726, and activates one or more discharge switches 732 completing a second circuit connecting the charged capacitor 730 and at least a portion of the individual 708 disposed between defibrillation electrodes 734.

The energy is discharged from the defibrillation electrodes 734 in the form of a defibrillation shock. For example, the defibrillation electrodes 734 are connected to the skin of the individual 708 and located at positions on different sides of the heart of the individual 708, such that the defibrillation shock is applied across the heart of the individual 708. The defibrillation shock, in various examples, depolari7es a significant number of heart cells in a short amount of time. The defibrillation shock, for example, interrupts the propagation of the shockable rhythm (e.g., VF or V-Tach) through the heart. In some examples, the defibrillation shock is 200 J or greater with a duration of about 0.015 seconds. In some cases, the defibrillation shock has a multiphasic (e.g., biphasic) waveform. The discharge switch(es) 732 are controlled by the processor(s) 712, for example. In various implementations, the defibrillation electrodes 734 are connected to defibrillation leads 736. The defibrillation leads 736 are connected to a defibrillation port 738, in implementations. According to various examples, the defibrillation leads 736 are removable from the defibrillation port 738. For example, the defibrillation leads 736 are plugged into the defibrillation port 738.

In various implementations, the processor(s) 712 is operably connected to one or more transceivers 740 that transmit and/or receive data over one or more communication networks 742. For example, the transceiver(s) 740 includes a network interface card (NIC), a network adapter, a local area network (LAN) adapter, or a physical, virtual, or logical address to connect to the various external devices and/or systems. In various examples, the transceiver(s) 740 includes any sort of wireless transceivers capable of engaging in wireless communication (e.g., radio frequency (RF) communication). For example, the communication network(s) 742 includes one or more wireless networks that include a $3^{rd}$ Generation Partnership Project (3GPP) network, such as a Long Term Evolution (LTE) radio access network (RAN) (e.g., over one or more LTE bands), a New Radio (NR) RAN (e.g., over one or more NR bands), or a combination thereof. In some cases, the transceiver(s) 740 includes other wireless modems, such as a modem for engaging in WI-FI®, WIGIG®, WIMAX®, BLU-ETOOTH®, or infrared communication over the communication network(s) 742.

The defibrillator 700 is configured to transmit and/or receive data (e.g., ECG data, impedance data, data indicative of one or more detected heart rhythms of the individual 708, data indicative of one or more defibrillation shocks administered to the individual 708, etc.) with one or more external devices 744 via the communication network(s) 742. The external devices 744 include, for instance, mobile devices (e.g., mobile phones, smart watches, etc.), Internet of Things (IoT) devices, medical devices, computers (e.g., laptop devices, servers, etc.), or any other type of computing device configured to communicate over the communication network(s) 742. In some examples, the external device(s) 744 is located remotely from the defibrillator 700, such as at a remote clinical environment (e.g., a hospital). According to various implementations, the processor(s) 712 causes the transceiver(s) 740 to transmit data to the external device(s) 744. In some cases, the transceiver(s) 740 receives data from the external device(s) 744 and the transceiver(s) 740 provide the received data to the processor(s) 712 for further analysis.

In various implementations, the external defibrillator 700 also includes a housing 746 that at least partially encloses other elements of the external defibrillator 700. For example, the housing 746 encloses the detection circuit 710, the processor(s) 712, the memory 714, the charging circuit 722, the transceiver(s) 740, or any combination thereof. In some cases, the input device(s) 718 and output device(s) 720 extend from an interior space at least partially surrounded by the housing 746 through a wall of the housing 746. In various examples, the housing 746 acts as a barrier to moisture, electrical interference, and/or dust, thereby protecting various components in the external defibrillator 700 from damage.

In some implementations, the external defibrillator 700 is an automated external defibrillator (AED) operated by an untrained user (e.g., a bystander, layperson, etc.) and can be operated in an automatic mode. In automatic mode, the processor(s) 712 automatically identifies a rhythm in the ECG signal, makes a decision whether to administer a defibrillation shock, charges the capacitor(s) 730, discharges the capacitor(s) 730, or any combination thereof. In some cases, the processor(s) 712 controls the output device(s) 720 to output (e.g., display) a simplified user interface to the untrained user. For example, the processor(s) 712 refrains from causing the output device(s) 720 to display a waveform of the ECG signal and/or the impedance signal to the untrained user, in order to simplify operation of the external defibrillator 700.

In some examples, the external defibrillator 700 is a monitor-defibrillator utili7ed by a trained user (e.g., a clinician, an emergency responder, etc.) and can be operated in a manual mode or the automatic mode. When the external defibrillator 700 operates in manual mode, the processor(s) 712 cause the output device(s) 720 to display a variety of information that may be relevant to the trained user, such as waveforms indicating the ECG data and/or impedance data, notifications about detected heart rhythms, and the like.

Figure 8:
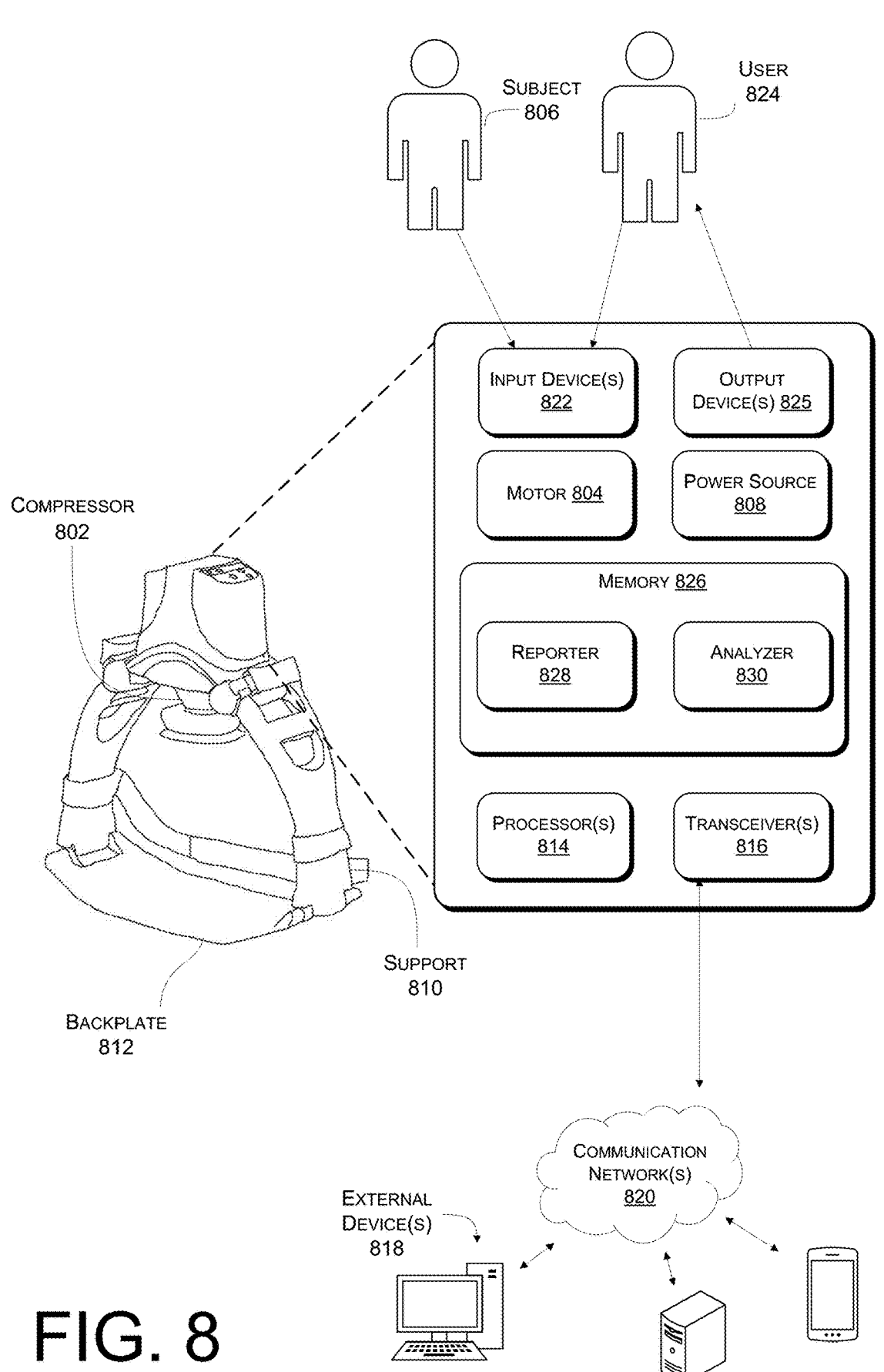
FIG. 8 illustrates a chest compression device configured to perform various functions described herein.

FIG. 8 illustrates a chest compression device 800 configured to perform various functions described herein. For example, the chest compression device 800 is the monitoring device 106 or the treating device 110 described in FIG. 1.

In various implementations, the chest compression device 800 includes a compressor 802 that is operatively coupled to a motor 804. The compressor 802 physically administers a force to the chest of a subject 806 that compresses the chest of the subject 806. In some examples, the compressor 802 includes at least one piston that periodically moves between two positions (e.g., a compressed position and a release position) at a compression frequency. For example, when the piston is positioned on the chest of the subject 806, the piston compresses the chest when the piston is moved into the compressed position. A suction cup may be positioned on a tip of the piston, such that the suction cup contacts the chest of the subject 806 during operation. In various cases, the compressor 802 includes a band that periodically tightens to a first tension and loosens to a second tension at a compression frequency. For instance, when the band is disposed around the chest of the subject 806, the band compresses the chest when the band tightens.

The motor 804 is configured to convert electrical energy stored in a power source 808 into mechanical energy that moves and/or tightens the compressor 802, thereby causing the compressor 802 to administer the force to the chest of the subject 806. In various implementations, the power source 808 is portable. For instance, the power source 808 includes at least one rechargeable (e.g., lithium-ion) battery. In some cases, the power source 808 supplies electrical energy to one or more elements of the chest compression device 800 described herein.

In various cases, the chest compression device 800 includes a support 810 that is physically coupled to the compressor 802, such that the compressor 802 maintains a position relative to the subject 806 during operation. In some implementations, the support 810 is physically coupled to a backplate 812, cot, or other external structure with a fixed position relative to the subject 806. According to some cases, the support 810 is physically coupled to a portion of the subject 806, such as wrists of the subject 806.

The operation of the chest compression device 800 may be controlled by at least one processor 814. In various implementations, the motor 804 is communicatively coupled to the processor(s) 814. Specifically, the processor(s) 814 is configured to output a control signal to the motor 804 that causes the motor 804 to actuate the compressor 802. For instance, the motor 804 causes the compressor 802 to administer the compressions to the subject 806 based on the control signal. In some cases, the control signal indicates one or more treatment parameters of the compressions. Examples of treatment parameters include a frequency, timing, depth, force, position, velocity, and acceleration of the compressor 802 administering the compressions. According to various cases, the control signal causes the motor 804 to cease compressions.

In various implementations, the chest compression device 800 includes at least one transceiver 816 configured to communicate with at least one external device 818 over one or more communication networks 820. Any communication network described herein can be included in the communication network(s) 820 illustrated in FIG. 8. The external device(s) 818, for example, includes at least one of a monitor-defibrillator, an AED, an ECMO device, a ventilation device, a patient monitor, a mobile phone, a server, or a computing device. In some implementations, the transceiver(s) 816 is configured to communicate with the external device(s) 818 by transmitting and/or receiving signals wirelessly. For example, the transceiver(s) 816 includes a NIC, a network adapter, a LAN adapter, or a physical, virtual, or logical address to connect to the various external devices and/or systems. In various examples, the transceiver(s) 816 includes any sort of wireless transceivers capable of engaging in wireless communication (e.g., RF communication). For example, the communication network(s) 820 includes one or more wireless networks that include a 3GPP network, such as an LTE RAN (e.g., over one or more LTE bands), an NR RAN (e.g., over one or more NR bands), or a combination thereof. In some cases, the transceiver(s) 816 includes other wireless modems, such as a modem for engaging in WI-FI®, WIGIG®, WIMAX®, BLUETOOTH®, or infrared communication over the communication network(s) 820. The signals, in various cases, encode data in the form of data packets, datagrams, or the like. In some cases, the signals are transmitted as compressions are being administered by the chest compression device 800 (e.g., for real-time feedback by the external device(s) 818), after compressions are administered by the chest compression device 800 (e.g., for post-event review at the external device 818), or a combination thereof.

In various cases, the processor(s) 814 generates the control signal based on data encoded in the signals received from the external device(s) 818. For instance, the signals include an instruction to initiate the compressions, and the processor(s) 814 instructs the motor 806 to begin actuating the compressor 802 in accordance with the signals.

In some cases, the chest compression device 800 includes at least one input device 822. In various examples, the input device(s) 822 is configured to receive an input signal from a user 824, who may be a rescuer treating the subject 806. Examples of the input device(s) 822 include, for instance, at a keypad, a cursor control, a touch-sensitive display, a voice input device (e.g., a microphone), a haptic feedback device (e.g., a gyroscope), an accelerometer, or any combination thereof. In various implementations, the processor(s) 814 generate the control signal based on the input signal. For instance, the processor(s) 814 generate the control signal to adjust a frequency of the compressions based on the chest compression device 800 detecting a selection by the user 824 of a user interface element displayed on a touchscreen or detecting the user 824 pressing a button integrated with an external housing of the chest compression device 800.

According to some examples, the input device(s) 822 include one or more sensors. The sensor(s), for example, is configured to detect a physiological parameter of the subject 806. In some implementations, the sensor(s) is configured to detect a state parameter of the chest compression device 800, such as a position of the compressor 802 with respect to the subject 806 or the backplate 812, a force administered by the compressor 802 on the subject 806, a force administered onto the backplate 812 by the body of the subject 806 during a compression, or the like. According to some implementations, the signals transmitted by the transceiver(s) 816 indicate the physiological parameter(s) and/or the state parameter(s).

The chest compression device 800 further includes at least one output device 825, in various implementations. Examples of the output device(s) 825 include, for instance, least one of a display (e.g., a projector, an LED screen, etc.), a speaker, a haptic output device, a printer, or any combination thereof. In some implementations, the output device(s) 825 include a screen configured to display various parameters detected by and/or reported to the chest compression device 800, a charge level of the power source 808, a timer indicating a time since compressions were initiated or paused, and other relevant information.

The chest compression device 800 further includes memory 826. In various implementations, the memory 826 is volatile (such as random access memory (RAM)), nonvolatile (such as read only memory (ROM), flash memory, etc.) or some combination of the two. The memory 826 stores instructions that, when executed by the processor(s) 814, causes the processor(s) 814 to perform various operations. In various examples, the memory 826 stores methods, threads, processes, applications, objects, modules, any other sort of executable instruction, or a combination thereof. In some cases, the memory 826 stores files, databases, or a combination thereof. In some examples, the memory 826 includes, but is not limited to, RAM, ROM, EEPROM, flash memory, or any other memory technology. In some examples, the memory 826 includes one or more of CD-ROMs, DVDs, CAM, or other optical storage, magnetic cassettes, magnetic tape, magnetic disk storage or other magnetic storage devices, or any other medium which can be used to store the desired information. In various cases, the memory 826 stores instructions, programs, threads, objects, data, or any combination thereof, that cause the processor(s) 814 to perform various functions. In various cases, the memory 826 stores one or more parameters that are detected by the chest compression device 800 and/or reported to the chest compression device 800.

In implementations of the present disclosure, the memory 826 also stores instructions for executing a reporter 828 and analyzer 830. The processor(s) 814, when executing the reporter 828, may be configured to generate communication signals to communicate treatment parameters to an external device, wherein the communication signals are output by the transceiver(s) 816. In various cases, the analyzer 830 causes the processor(s) 814 to analyze data generated by the input device(s) 822.

EXAMPLE CLAUSES

1. A monitor-defibrillator, including: a detection circuit configured to detect an electrocardiogram (ECG) signal of a subject; an analog-to-digital converter (ADC) configured to convert the ECG signal into unfiltered ECG data; a display; an input device configured to receive a first input signal and a second input signal from a rescuer; a discharge circuit configured to output an electrical shock to the subject; and a processor configured to: cause the display to visually present the unfiltered ECG data; determine that a mechanical chest compression device is administering chest compressions to the subject at a frequency; in response to determining that the mechanical chest compression device is administering the chest compressions to the subject at the frequency: generate filtered ECG data by applying a comb filter to the unfiltered ECG data, the comb filter rejecting the frequency and harmonics of the frequency; cause the display to visually present a message indicating that the filtered ECG data is available; and in response to the input device receiving the first input signal, cause the display to visually present the filtered ECG data; determine that the filtered ECG data is indicative of ventricular fibrillation (VF); and in response to determining that the filtered ECG data is indicative of VF: cause the display to visually present an instruction to defibrillate the subject; and in response to the input device receiving the second input signal, cause the discharge circuit to output the electrical shock.

2. The monitor-defibrillator of clause 1, wherein the processor is configured to cause the display to visually present the filtered ECG data by: causing the display to output a first waveform representing the unfiltered ECG data at a first emphasis; and causing the display to output a second waveform representing the filtered ECG data at a second emphasis, the second emphasis being greater than the first emphasis.

3. The monitor-defibrillator of clause 1 or 2, further including: a transceiver configured to receive a communication signal from the mechanical chest compression device, wherein the processor is configured to determine that the mechanical chest compression device is administering the chest compressions to the subject in response to the transceiver receiving the communication signal, and wherein the processor is further configured to generate the comb filter by analyzing the communication signal.

4. The monitor-defibrillator of any one of clauses 1 to 3, wherein the processor is configured to determine that the mechanical chest compression device is administering the chest compressions to the subject by: detecting an artifact associated with the chest compressions in the unfiltered ECG data; and determining that a shape of the artifact is associated with the mechanical chest compression device.

5. A method performed by a first medical device, the method including: generating first data indicating a physiological parameter of a subject; generating a filter configured to remove an artifact associated with a treatment; generating second data by applying the filter to the first data; determining that a second medical device is administering the treatment to the subject; and in response to determining that the second medical device is administering the treatment to the subject: outputting an indication that filtering is available; receiving an input signal selecting the filtering; and in response to receiving the input signal, displaying the second data.

6. The method of clause 5, wherein the physiological parameter includes wherein the physiological parameter includes an electrocardiogram (ECG), a capnograph, a transthoracic impedance, a force administered to a user, a blood pressure, an airway parameter, a partial pressure of oxygen, an electroencephalogram (EEG), a temperature, a blood flow, or a pulse rate.

7. The method of clause 5 or 6, wherein the treatment includes chest compressions, and wherein the filter includes a comb filter rejecting a frequency of the chest compressions and harmonics of the frequency of the chest compressions.

8. The method of clause 7, further including: determining the frequency of the chest compressions by receiving a communication signal from the second medical device.

9. The method of clause 7 or 8, further including: determining the frequency of the chest compressions by identifying an artifact associated with the chest compressions in the first data.

10. The method of any one of clauses 5 to 9, further including: in response to receiving the input signal, displaying a first waveform representing the first data at a first emphasis, wherein displaying the second data includes displaying a second waveform representing the second data at a second emphasis, the second waveform overlapping the first waveform, the second emphasis being greater than the first emphasis.

11. The method of clause 10, wherein the first waveform includes a different color than the second waveform, the first waveform includes a different contrast than the second waveform, the first waveform includes a different line size than the second waveform, the first waveform includes a different transparency than the second waveform, or the first waveform includes a different line style than the second waveform.

12. The method any one of clauses 5 to 11, further including: determining that the second medical device has discontinued the treatment to the subject; and in response to determining that the second medical device has discontinued the treatment to the subject, displaying the first data.

13. A first medical device, including: an input device configured to detect an input signal; an output device; and a processor configured to: generate first data indicating a physiological parameter of a subject; generate a filter configured to remove an artifact associated with a treatment; generate second data by applying the filter to the first data; determine that a second medical device is administering the treatment to the subject; and in response to determining that the second medical device is administering the treatment to the subject: cause the output device to output an indication that filtering is available; and in response to the input device receiving the input signal, cause the output device to output the second data.

14. The first medical device of clause 13, wherein the input device includes a button, a touch sensor, or a microphone.

15. The first medical device of clause 13 or 14, wherein the output device includes a display, a light, or a speaker.

16. The first medical device of any one of clauses 13 to 15, wherein the output device includes a display, wherein the processor is further configured to cause the display to visually present a first waveform representing the first data at a first emphasis; and wherein the processor is configured to cause the output device to output the second data by causing the display to visually present a second waveform representing the second data at a second emphasis, the second waveform overlaying the first waveform, the second emphasis being greater than the first emphasis.

17. The first medical device of clause 16, wherein the first waveform includes a different color than the second waveform, the first waveform includes a different contrast than the second waveform, the first waveform includes a different line size than the second waveform, the first waveform includes a different transparency than the second waveform, or the first waveform includes a different line style than the second waveform.

18. The first medical device of any one of clauses 13 to 17, wherein the processor is further configured to: determine that the second medical device has paused administering the treatment to the subject; and in response to determining that the second medical device has paused administering the treatment to the subject, causing the output device to output the first data without outputting the second data.

19. The first medical device of any one of clauses 13 to 18, further including: a transceiver configured to receive a communication signal from the second medical device, wherein the processor is configured to determine that the second medical device is administering the treatment to the subject in response to the second medical device receiving the communication signal.

20. The first medical device of clause 19, wherein the communication signal indicates a treatment parameter characterizing the treatment administered to the subject, and wherein the processor is configured to generate the filter based on the treatment parameter.

21. A monitor-defibrillator, including: a detection circuit configured to detect an electrocardiogram (ECG) signal of a subject; an analog-to-digital converter (ADC) configured to convert the ECG signal into unfiltered ECG data; a display; an input device configured to receive a first input signal and a second input signal from a rescuer; a discharge circuit configured to output an electrical shock to the subject; and a processor configured to: generate filtered ECG data by applying a comb filter to the unfiltered ECG data, the comb filter rejecting a frequency at which a mechanical chest compression device is administering chest compressions to the subject; in response to the input device receiving the first input signal, cause the display to visually present the filtered ECG data; determine that the mechanical chest compression device has paused administering the chest compressions to the subject; in response to determining that the mechanical chest compression device has paused administering the chest compressions to the subject, automatically causing the display to visually present the unfiltered ECG data without visually presenting the filtered ECG data; determine that the unfiltered ECG data or the filtered ECG data is indicative of ventricular fibrillation; and in response to determining that the unfiltered ECG data or the filtered ECG is indicative of VF and the input device receiving the second input signal, cause the discharge circuit to output the electrical shock to the subject.

22. The monitor-defibrillator of clause 21, wherein the processor is configured to cause the display to visually present the filtered ECG data by: causing the display to output a first waveform representing the unfiltered ECG data at a first emphasis; and causing the display to output a second waveform representing the filtered ECG data at a second emphasis, the second emphasis being greater than the first emphasis.

23. The monitor-defibrillator of clause 21 or 22, further including: a transceiver configured to receive a communication signal from the mechanical chest compression device, wherein the processor is configured to determine that the mechanical chest compression device has paused administering the chest compressions to the subject in response to the transceiver receiving the communication signal.

24. The monitor-defibrillator of any one of clauses 21 to 23, wherein the processor is configured to determine that the mechanical chest compression device has paused administering the chest compressions to the subject by: determining that a chest compression artifact is absent from the unfiltered ECG data.

25. A method performed by a first medical device, the method including: generating first data indicating a physiological parameter of a subject; generating a filter configured to remove an artifact associated with a treatment; generating second data by applying the filter to the first data; receiving an input signal; in response to receiving the input signal, displaying the second data; determining that a second medical device has paused the treatment; and in response to determining that the second medical device has paused the treatment, displaying the first data without displaying the second data.

26. The method of clause 25, wherein the physiological parameter includes wherein the physiological parameter includes an electrocardiogram (ECG), a capnograph, a transthoracic impedance, a force administered to a user, a blood pressure, an airway parameter, a partial pressure of oxygen, an electroencephalogram (EEG), a temperature, a blood flow, or a pulse rate.

27. The method of clause 25 or 26, wherein the treatment includes chest compressions, and wherein the filter includes a comb filter rejecting a frequency of the chest compressions and harmonics of the frequency of the chest compressions.

28. The method of clause 27, further including: determining the frequency of the chest compressions by: receiving a signal from the second medical device; or analyzing the first data.

29. The method of any one of clauses 25 to 28, further including: in response to receiving the input signal, displaying a first waveform representing the first data at a first emphasis, wherein displaying the second data includes displaying a second waveform representing the second data at a second emphasis, the second waveform overlapping the first waveform, the second emphasis being greater than the first emphasis.

30. The method of clause 29, wherein the first waveform includes a different color than the second waveform, the first waveform includes a different contrast than the second waveform, the first waveform includes a different line size than the second waveform, the first waveform includes a different transparency than the second waveform, or the first waveform includes a different line style than the second waveform.

31. The method of any one of clauses 25 to 30, wherein determining that the second medical device has paused administering the treatment to the subject includes: receiving, from the second medical device, a communication signal.

32. The method of any one of clauses 25 to 31, wherein determining that the second medical device has paused administering the treatment to the subject includes: determining that an artifact associated with the treatment is absent from the first data.

33. A first medical device, including: an input device configured to detect an input signal; an output device; and a processor configured to: generate first data indicating a physiological parameter of a subject; generate a filter configured to remove an artifact associated with a treatment; generate second data by applying the filter to the first data; cause the output device to output an indication that filtering is available; in response to the input device receiving the input signal, cause the output device to output the second data; determine that a second medical device has paused administering the treatment to the subject; and in response to determining that the second medical device has paused administering the treatment to the subject, cause the output device to output the first data without outputting the second data.

34. The first medical device of clause 33, wherein the input device includes a button, a touch sensor, or a microphone.

35. The first medical device of clause 33 or 34, wherein the output device includes a display, a light, or a speaker.

36. The first medical device of any one of clauses 33 to 35, wherein the output device includes a display, wherein the processor is configured to cause the output device to output the second data by: causing the display visually present a first waveform representing the first data at a first emphasis; and causing the display to visually present a second waveform representing the second data at a second emphasis, the second waveform overlaying the first waveform, the second emphasis being greater than the first emphasis.

37. The first medical device of any one of clauses 33 to 36, wherein the processor is configured to determine that the second medical device has paused administering the treatment to the subject by determining that an artifact associated with the artifact is absent from the first data.

38. The first medical device of any one of clauses 33 to 37, further including: a transceiver configured to receive a communication signal from the second medical device, wherein the processor is configured to determine that the second medical device has paused administering the treatment to the subject in response to the second medical device receiving the communication signal.

39. The first medical device of clause 38, wherein the communication signal indicates a treatment parameter characterizing the treatment administered to the subject, and wherein the processor is configured to generate the filter based on the treatment parameter.

40. The first medical device of clause 38 or 39, wherein the processor is further configured to: determine that the communication signal has been interrupted, and wherein the processor is configured to cause the output device to output the first data without outputting the second data further in response to determining that the communication signal has been interrupted.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventors expect skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

What is claimed is:

1. A monitor-defibrillator, comprising:
a detection circuit configured to detect an electrocardio-gram (ECG) signal of a subject;
an analog-to-digital converter (ADC) configured to convert the ECG signal into unfiltered ECG data;
a display;
an input device configured to receive a first input signal and a second input signal from a rescuer;
a discharge circuit configured to output an electrical shock to the subject; and
a processor configured to:
cause the display to visually present the unfiltered ECG data;
determine that a mechanical chest compression device is administering chest compressions to the subject at a frequency;
in response to determining that the mechanical chest compression device is administering the chest compressions to the subject at the frequency:
generate filtered ECG data by applying a comb filter to the unfiltered ECG data, the comb filter rejecting the frequency and harmonics of the frequency;
cause the display to visually present a message indicating that the filtered ECG data is available; and
in response to the input device receiving the first input signal, cause the display to visually present the filtered ECG data;
determine that the filtered ECG data is indicative of ventricular fibrillation (VF); and
in response to determining that the filtered ECG data is indicative of VF:
cause the display to visually present an instruction to defibrillate the subject; and
in response to the input device receiving the second input signal, cause the discharge circuit to output the electrical shock.

2. The monitor-defibrillator of claim 1, wherein the processor is configured to cause the display to visually present the filtered ECG data by:
causing the display to output a first waveform representing the unfiltered ECG data at a first emphasis; and
causing the display to output a second waveform representing the filtered ECG data at a second emphasis, the second emphasis being greater than the first emphasis.

3. The monitor-defibrillator of claim 1, further comprising:
a transceiver configured to receive a communication signal from the mechanical chest compression device,
wherein the processor is configured to determine that the mechanical chest compression device is administering the chest compressions to the subject in response to the transceiver receiving the communication signal, and
wherein the processor is further configured to generate the comb filter by analyzing the communication signal.

4. The monitor-defibrillator of claim 1, wherein the processor is configured to determine that the mechanical chest compression device is administering the chest compressions to the subject by:

detecting an artifact associated with the chest compressions in the unfiltered ECG data; and
determining that a shape of the artifact is associated with the mechanical chest compression device.

5. A method performed by a first medical device, the method comprising:
generating first data indicating a physiological parameter of a subject;
generating a filter configured to remove an artifact associated with a treatment;
generating second data by applying the filter to the first data;
determining that a second medical device is administering the treatment to the subject; and
in response to determining that the second medical device is administering the treatment to the subject:
outputting an indication that filtering is available;
receiving an input signal selecting the filtering; and
in response to receiving the input signal, displaying the second data.

6. The method of claim 5, wherein the physiological parameter comprises wherein the physiological parameter comprises an electrocardiogram (ECG), a capnograph, a transthoracic impedance, a force administered to a user, a blood pressure, an airway parameter, a partial pressure of oxygen, an electroencephalogram (EEG), a temperature, a blood flow, or a pulse rate.

7. The method of claim 5, wherein the treatment comprises chest compressions, and
wherein the filter comprises a comb filter rejecting a frequency of the chest compressions and harmonics of the frequency of the chest compressions.

8. The method of claim 7, further comprising:
determining the frequency of the chest compressions by receiving a communication signal from the second medical device.

9. The method of claim 7, further comprising:
determining the frequency of the chest compressions by identifying an artifact associated with the chest compressions in the first data.

10. The method of claim 5, further comprising:
in response to receiving the input signal, displaying a first waveform representing the first data at a first emphasis,
wherein displaying the second data comprises displaying a second waveform representing the second data at a second emphasis, the second waveform overlapping the first waveform, the second emphasis being greater than the first emphasis.

11. The method of claim 10, wherein the first waveform comprises a different color than the second waveform, the first waveform comprises a different contrast than the second waveform, the first waveform comprises a different line size than the second waveform, the first waveform comprises a different transparency than the second waveform, or the first waveform comprises a different line style than the second waveform.

12. The method of claim 5, further comprising:
determining that the second medical device has discontinued the treatment to the subject; and
in response to determining that the second medical device has discontinued the treatment to the subject, displaying the first data.

13. A first medical device, comprising:

an input device configured to detect an input signal;

an output device; and a processor configured to:

generate first data indicating a physiological parameter of a subject;

generate a filter configured to remove an artifact associated with a treatment;

generate second data by applying the filter to the first data;

determine that a second medical device is administering the treatment to the subject; and in response to determining that the second medical device is administering the treatment to the subject:

cause the output device to output an indication that filtering is available; and in response to the input device receiving the input signal, cause the output device to output the second data.

14. The first medical device of claim 13, wherein the input device comprises a button, a touch sensor, or a microphone.

15. The first medical device of claim 13, wherein the output device comprises a display, a light, or a speaker.

16. The first medical device of claim 13, wherein the output device comprises a display, wherein the processor is further configured to cause the display to visually present a first waveform representing the first data at a first emphasis; and wherein the processor is configured to cause the output device to output the second data by causing the display to visually present a second waveform representing the second data at a second emphasis, the second waveform overlaying the first waveform, the second emphasis being greater than the first emphasis.

17. The first medical device of claim 16, wherein the first waveform comprises a different color than the second waveform, the first waveform comprises a different contrast than the second waveform, the first waveform comprises a different line size than the second waveform, the first waveform comprises a different transparency than the second waveform, or the first waveform comprises a different line style than the second waveform.

18. The first medical device of claim 13, wherein the processor is further configured to:

determine that the second medical device has paused administering the treatment to the subject; and in response to determining that the second medical device has paused administering the treatment to the subject, causing the output device to output the first data without outputting the second data.

19. The first medical device of claim 13, further comprising:

a transceiver configured to receive a communication signal from the second medical device, wherein the processor is configured to determine that the second medical device is administering the treatment to the subject in response to the second medical device receiving the communication signal.

20. The first medical device of claim 19, wherein the communication signal indicates a treatment parameter characterizing the treatment administered to the subject, and wherein the processor is configured to generate the filter based on the treatment parameter.

\* \* \* \* \*